United States Patent [19]

Marogil

[11] Patent Number: 5,304,188
[45] Date of Patent: Apr. 19, 1994

[54] SURGICAL CLAMP AND METHOD

[76] Inventor: Joseph B. Marogil, 2151 Robinson Road, SE., Grand Rapids, Mich. 49506-1876

[21] Appl. No.: 9,125

[22] Filed: Jan. 26, 1993

[51] Int. Cl.$^5$ ............................................. A61B 17/00
[52] U.S. Cl. ................... 606/157; 24/16 PB
[58] Field of Search ............ 606/151, 157, 158, 201, 606/203, 232; 24/16 PB, 49 S; 128/898

[56] References Cited

U.S. PATENT DOCUMENTS

| | | | |
|---|---|---|---|
| 3,339,247 | 9/1967 | Geisinger | 24/16 PB |
| 3,577,601 | 3/1969 | Mariani | 24/16 PB |
| 3,744,096 | 7/1973 | Kok | 24/16 PB |
| 3,857,396 | 12/1974 | Hardwick | 606/232 |
| 3,991,444 | 11/1976 | Bailey | 24/16 PB |
| 4,128,100 | 12/1978 | Wendorff | 606/157 |
| 4,377,887 | 3/1983 | Valestin | 24/206 R |
| 4,439,902 | 4/1984 | Huxtable | 24/278 |
| 4,558,699 | 12/1985 | Bashour . | |
| 4,573,242 | 3/1986 | Lankton et al. | 24/16 PB |
| 4,862,560 | 9/1989 | Lichtenberg | 24/16 PB |
| 4,882,813 | 11/1989 | Nakamura | 24/16 PB |
| 4,955,913 | 9/1990 | Robinson | 606/228 |

FOREIGN PATENT DOCUMENTS 2063354A 6/1981 United Kingdom .

OTHER PUBLICATIONS

Tien-Yu Lin, Ann. Surg., "Results in 107 Hepatic Lobectomies with a Preliminary Report on the Use of a Clamp to Reduct Blook Loss," Apr., 1973, pp. 413-421.
Sergio Mies and Dr. Silvano Raia, Surgery, Gynecology and Obstetrics "A Simple Method for Controlling Hemorrhage During Hepatectomy," Mar. 1989 pp. 265-266.
Benad Goldwasser, Bert A. Bowers, Culley C. Carbon, III, & William C. Meyers, Surgery, Gynecology and Obstetrics, "A New Clamp for Hepatic Resection," Apr. 1987, 379-80.
Takashi Kanematsu, et al., Japanese Journal of Surgery, vol. 14, No. 5, 1984, "A Newly Designed Clamp Facilitates Hepatic Resection," Mar. 1984, pp. 432-433.

*Primary Examiner*—Tamara L. Graysay
*Attorney, Agent, or Firm*—Varnum, Riddering, Schmidt & Howlett

[57] ABSTRACT

This relates to a surgical clamp which is of a simple construction, which may be readily utilized and is readily disposable. The surgical clamp is intended for being passed around and clamping off a portion of a solid organ such as a liver, kidney or any other solid organ. The surgical clamp is simply in the form of a plastic strap having two free ends. The strap is passed around the organ to clamp off the desired portion of the organ, after which the free ends of the strap are passed through openings in a clip having latch members for engaging the strap and retaining it in a tight position. The clip is then moved up onto the strap so as to tighten the strap around the organ and to clamp the organ sufficiently to prevent or greatly restrict bleeding. The clip includes latch members which automatically operate to hold the strap in an organ clamping position. The latch members are provided with manual releases so as to permit the reverse movement of the clip on the strap portions and the removal of the surgical clamp from the affected organ. With a portion of the affected organ clamped off, the affected portion of the organ is readily observable and is ready for a required surgical procedure without the undue flow and resulting loss of blood which may restrict the surgical procedure.

17 Claims, 3 Drawing Sheets

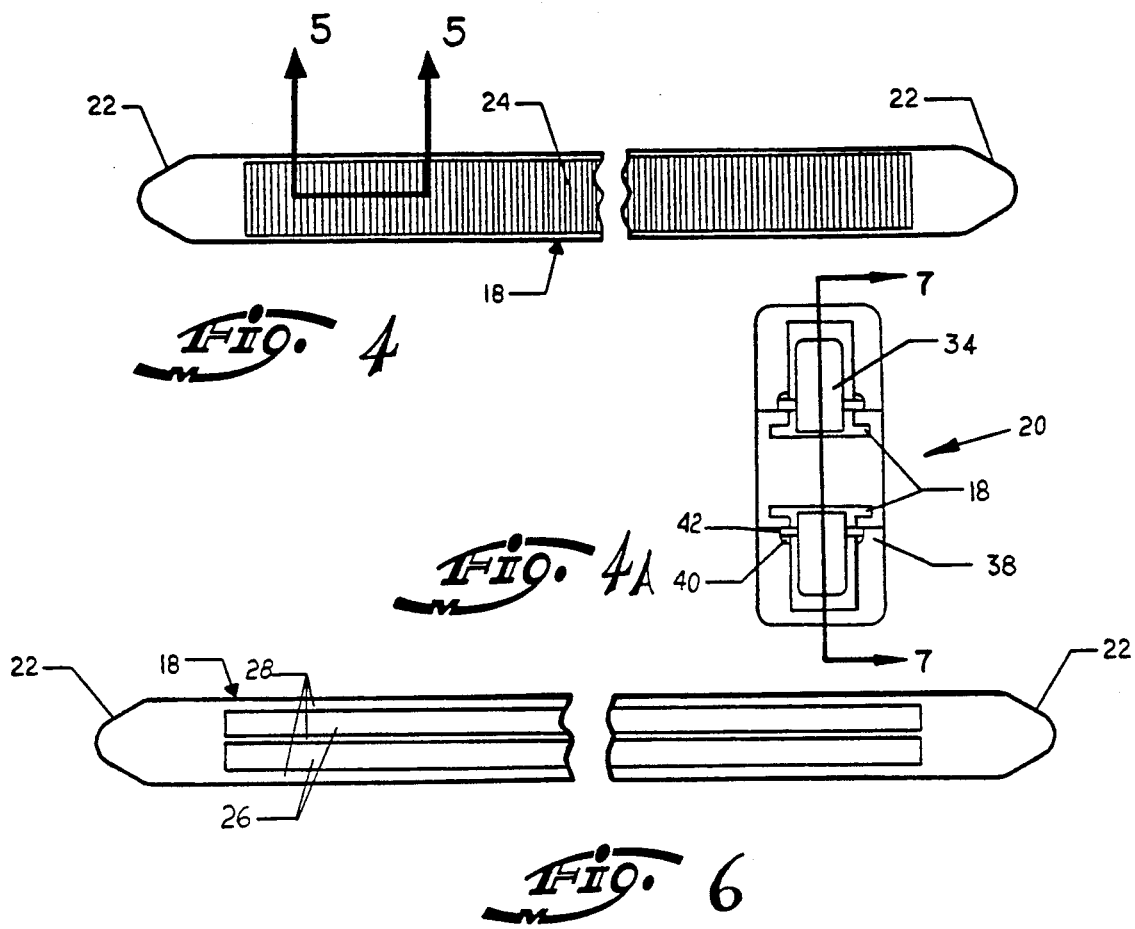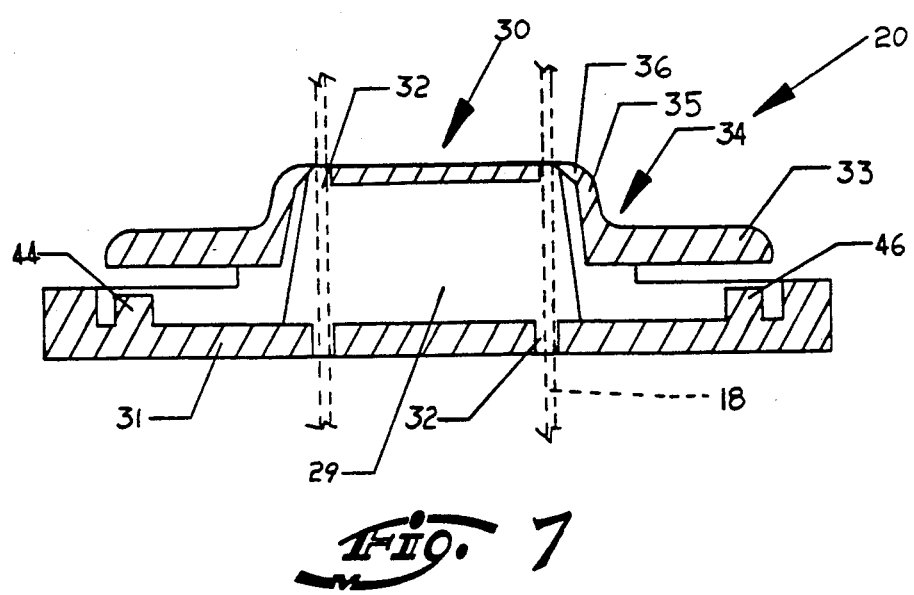

SURGICAL CLAMP AND METHOD

This invention relates in general to new and useful improvements in surgical clamps, and more particularly to a surgical clamp which may be readily applied to a solid organ such as the liver, kidney or other solid organ to clamp off a portion of such organ to generally shut off the flow of blood to a damaged area of such organ. The invention also relates to a method of clamping off a human organ in a surgical procedure.

BACKGROUND OF THE INVENTION

It is known to clamp off parts of organs such as the liver, kidney or other solid organ to stop bleeding so that a damaged portion of the organ may be readily observed without the presence of a significant amount of blood and the damaged area can be repaired without excessive bleeding.

It is known to provide a scissors-type clamp with a holding clip so as to clamp off a portion of an organ. However, such clamps must be specifically designed to engage a specific portion of such organ in order to provide an effective clamping action.

More recently, conventional cable clamps have been utilized to clamp off a portion of an organ in a surgical procedure. More specifically, two conventional cable clamps have been used in back-to-back relation with the strap of one cable clamp being passed through the clip of the other cable clamp so that the two straps work in unison. Such a strap like clamp, while being effective, is difficult to work and is time-consuming to apply.

SUMMARY OF THE INVENTION

The invention relates to a surgical clamp in the form of a single strap having a dual function clip for simultaneously receiving both ends of such strap whereby the strap may be readily applied to an organ, after which the clip may then be applied to both ends of the strap and the two ends of the strap are quickly drawn through the clip so as to tighten the strap about the organ. The surgical clamp is used to clamp off parts of organs such as the liver, kidney or other solid organ so as to restrict flow of blood into the clamped off portion of the organ. The surgical clamp may be utilized in conjunction with surgical procedures which take a great deal of time and are normally very difficult because of the flow of blood. The surgical clamp may also be used in trauma situations where there is damage to an organ. The surgical clamp is used to shut off the flow of blood to the damaged area so that the damaged area can be observed without the presence of a significant amount of blood and the damaged area can be repaired without undue bleeding.

The invention also relates to a method of clamping off a portion of an organ in a surgical procedure on such organ, the method comprising the steps of encircling a portion of an organ with a strap having two ends, applying a single clip to the two ends and drawing the two ends through the clip to tightly strap and clamp the organ to prevent flow of blood to a clamped-off portion of the organ. The clip preferably automatically locks the strap against return movement. The clip preferably comprises a molded plastic body having two adjacent parallel strap-receiving openings therethrough, each of the openings having projecting thereunto a latch member for engaging a like side of the strap to prevent reverse movement of the strap through each of the openings. The latch members preferably include transverse teeth for biting engagement with the strap. The latch members further preferably have a release facilitating member and the method comprises releasing the clip by depressing the release facilitating member.

The latch members according to the invention are L-shaped in cross section with one leg extending parallel to the opening and along the strap and having a strap-engaging distal end portion thereof. Another leg of the latch member extends rearwardly away from the strap to provide a release element for releasing the latch engagement with the strap. The latch members are relatively rigid so that each latch member moves as a unit. The latch members are mounted at a central portion of the body through torsion bars which extend laterally of the latch members. The torsion bars bias the latch members against the elongated strap and into the opening to resiliently prevent reverse movement of the strap through the body.

The invention provides a way in which an organ can be effectively clamped off quickly and easily and yet can be also released quickly and easily. The surgeon can usually assemble the strap by himself or herself and can release the strap with one hand if necessary.

With the above and other objects that will hereinafter appear, the nature of the invention will be more clearly understood by reference to the following detailed description, the appended claims, and the several views illustrated in the accompanying drawings.

IN THE DRAWINGS

The invention will now be described with reference to the drawings in which:

FIG. 4 is an plan view of the strap of the surgical clamp shown in FIG. 1, of the surgical clamp with portions of the strap being broken away; FIG. 4a is a plan view of the clip of the surgical clamp shown in FIG. 1;

FIG. 6 is a bottom plan view of the strap showing the configuration of an organ clamping side thereof, an intermediate portion of the strap being broken away;

FIG. 7 is a sectional view taken generally along the line 7—7 of FIG. 4a and shows the strap gripping mechanism of the clip; and FIG. 8 is a perspective view of the strap gripping mechanism of FIG. 4a.

DESCRIPTION OF PREFERRED EMBODIMENT OF INVENTION

Figure 1:
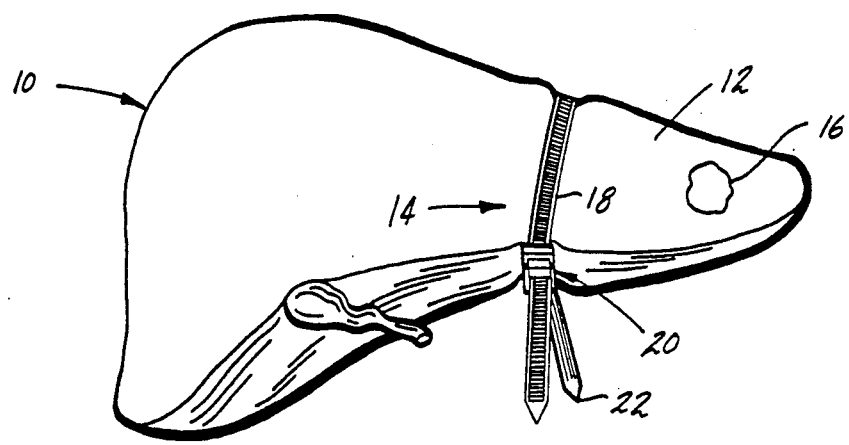
FIG. 1 is a perspective view of an organ, such as the human liver, having a portion thereof clamped off utilizing the surgical clamp.
Figure 2:
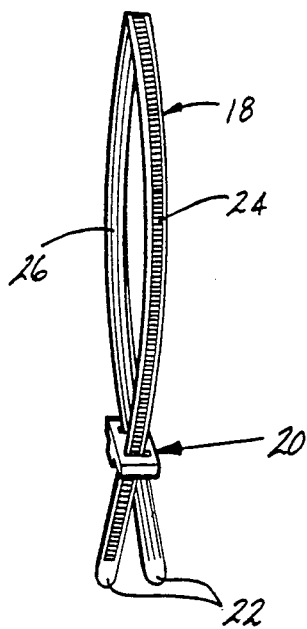
FIG. 2 is a front perspective of the surgical clamp shown in FIG. 1.
Figure 3:
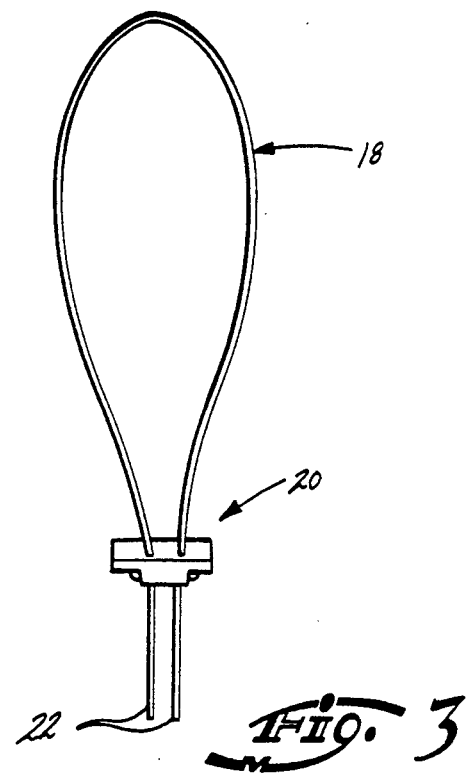
FIG. 3 is a side perspective view of the surgical clamp shown in FIG. 1.

Referring now to the drawings in detail, reference is first made to FIG. 1 wherein there is illustrated a human liver generally identified by the numeral 10. The liver 10 has a portion 12 thereof clamped off by way of a surgical clamp in accordance with this invention, the surgical clamp being generally identified by the numeral 14. The illustrated liver 10 has in the clamped off portion 12 a tumor 16 which is to be removed by way of a surgical procedure.

The surgical clamp 14 is of a two-piece construction and includes an elongated plastic strap 18 which is formed of a plastic, such as nylon, which is compatible with the human body. The surgical clamp 14 also includes a clip generally identified by the numeral 20 which is also primarily formed of a plastic which may be nylon or other plastic compatible with the human body.

Figure 5:
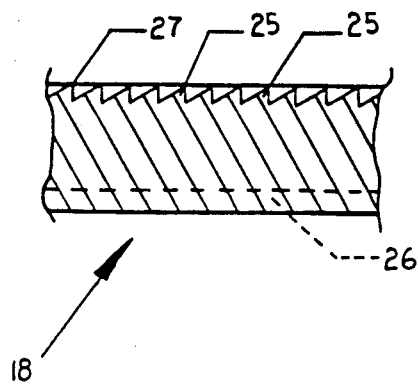
FIG. 5 is a sectional view taken generally along line 5—5 of FIG. 4 and shows the strap.

The strap 18 is provided with rounded ends 22 and a major portion of the strap 18 on one side or face, as shown in FIG. 4, is provided with a transverse groove and rib arrangement 24 for interlocking engagement with the clip 20 as will be described in detail hereinafter. As shown in section in FIG. 5, the transverse groove and rib arrangement comprises a plurality of triangular shaped transverse ribs 25, each having an apex 27, generally oriented away from the rounded ends 22 of the strap 18.

Referring now to FIG. 6, it will be seen that the reverse side or face of the strap 18, that is the face which engages the organ 10, may either be smooth or may be provided with longitudinally extending grooves 26 which define a plurality of transversely adjacent, longitudinally extending ribs 28 to provide a good clamping action with the organ 10.

Figure 8:
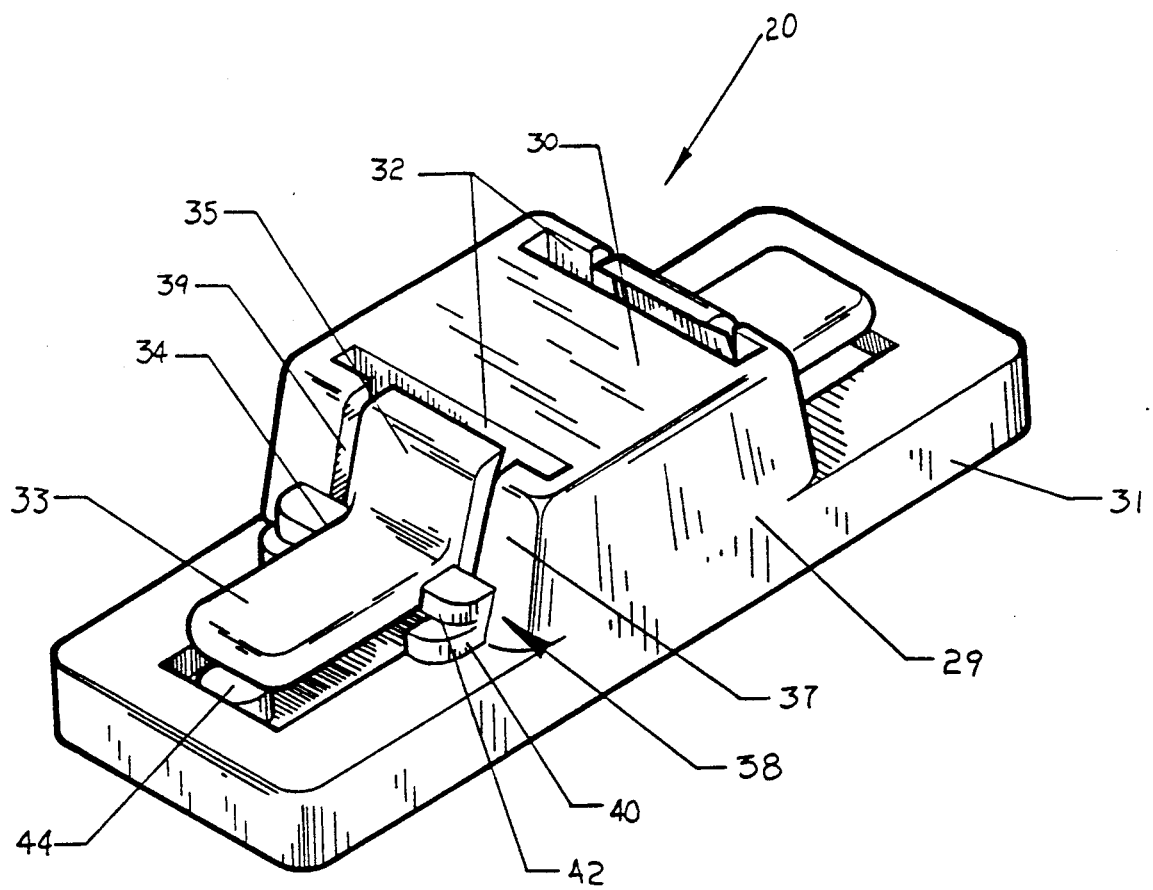

Referring now to FIGS. 7 and 8, it will be seen that the clip 20 is in the form of an integral molding including a body 30 having a raised central portion 29 and a flat base portion 31, with two longitudinal strap openings 32 through the flat base 31. The strap openings 32 are in transversely spaced, parallel relation and are of a size to receive the strap 14. A latch member 34 of L-shaped cross section, is associated with each of the strap openings 32, and comprises a horizontal leg 33, oriented along the body base portion 31, and vertical leg 35, oriented with the raised portion 29 of the body 30. A sharp ridge 36, at the end of the vertical portion 35, extends across, and into the strap opening 32 so as to bitingly engage the transverse rib and groove arrangement on the strap 18.

Each latch member 34 is resiliently hinged to the body 30 of the clip 20 by way of a hinge 38. The raised portion of the body 29 has sides 37 facing towards the base portion 31 as it extends away from the raised portion 29. Openings 39 in the raised portion sides 37 receive the vertical legs of the latch number 34. Each hinge 38 comprises a pair of pedestals 40, mounted on the base portion 31 where it meets the side 37, one on each side of the strap opening 32. A torsion bar 42 extends outwardly from each side of the latch member 34, at the intersection of its horizontal and vertical legs 33 and 35. The torsion bars 42 mount on the pedestals 40 to provide a limited degree of torsional rotative motion of the latch member 34 with respect to the body 30.

The plastic from which the clip 20 is constructed, is flexible enough to provide resilient torsional resistance of the spring-loaded latch member about the torsion bars 42. The natural position of the latch member 34 is with the ridge 36 extending into the strap opening 32, in a position to fit within the grooves between the transverse rib 25 of the strap 18. Downward pressure applied to the latch member horizontal leg 33 (toward the base 31), causes the ridge 36 to pivot away from the strap opening 32. A stop 44 can be provided on the base portion of the body 31, under each horizontal leg 33, to limit the rotation thereof.

With respect to FIG. 7, it is to be understood that the strap 18 can have each end portion thereof separately movable through the clip 20. Further, it is to be understood that in the illustrated relationship of FIG. 7, each strap portion is free to move upwardly with the strap 18, causing the respective latch member 34 to swing away from the strap opening 32 and to disengage the ridge 36 from transverse rib and groove arrangement 24 of the strap 18 (see also FIG. 5). On the other hand, when the strap portion 18 is to be moved downwardly, the teeth 36 dig into the transverse rib and groove arrangement 24 and movement of the strap 18 relative to the clip 20 is prevented.

It is to be understood that the clip 20 must be readily releasable from the strap 18 so as to facilitate the quick removal of the surgical clamp 14 from the organ. In order to release the associated strap portion 18, the horizontal leg 35 is pushed downwardly which moves the associated latch member 34 away from the opening 32 so as to release ridge 36 from the rib and groove arrangement 24 of the strap portion 18. This function is easily accomplished with one hand so that the physician can grip the organ with the other hand.

UTILIZATION OF SURGICAL CLAMP

Assuming that the affected organ is the liver 10 of FIG. 1 and that the suspected area is the right portion of the liver 10 as shown in FIG. 1, the surgical clamp 14 is utilized by passing the strap 18 around the liver 10 in position to clamp off the suspected part of the liver after which the two ends of the strap 18 are brought together and the clip 20 slid thereover. The clip 20 is then slid up on to the strap 18 to tightly clamp the strap 18 around the liver 10 to provide the necessary clamping action. This action is easily accomplished by holding the ends of the strap with one hand and pushing the clip up into tight engagement with the liver with the other hand.

The clamping action of the surgical clamp 14 serves to restrict the flow of blood to the clamped off portion of the liver 10 so that the liver 10 may be readily inspected with a minimum flow of blood. If a surgical procedure is required, for example, the removal of the tumor 16, this removal may be readily accomplished without a material loss of blood and without the flowing blood hindering the surgical procedure.

Of course, the removal of the tumor 16 from the liver 10 is only one of the many possible surgical procedures which would utilize the surgical clamp 14.

The surgical clamp 14 has a number of material advantages. First of all, it may be applied very quickly in a very simple manner. Secondly, it is adaptable to the contour of the organ so that no special clamp configuration is required. Thirdly, the movement of both straps ends 18 through the clip 20, allows the clamp 14 to be tightened without twisting the organ. Fourthly, it may be readily removed. In addition to the foregoing, it will be readily apparent that the surgical clamp is inexpensive and it is simple to sterilize and package.

The clip 20 is preferably made by injection molding from a thermoplastic resin such as polyethylene or polypropylene or polyvinyl chloride in one or two pieces. The strap can be injection molded from a similar material.

Although only a preferred embodiment of the surgical clamp and the utilization thereof have been specifically illustrated and described herein, it is to be understood that minor variations may be made in the surgical clamp and its usage without departing from the spirit and scope of the invention as disclosed herein. For instance other clip configurations are possible which retain the one way movement of both ends of the strap 18 through the clip 20, with easy releasability.

What is claimed as new is:

1. A surgical clamp for clamping off a portion of an organ to restrict bleeding during a surgical procedure while permitting normal blood flow to other portions of such organ, said surgical clamp comprising an elongated flexible plastic strap having two ends facilitating the encirclement of a portion of an organ, and a separately formed clip having a body portion with two adjacent openings therethrough receiving end portions of the strap and a spring-loaded latch member in each of the openings for latching end portions of the strap, each of the latch members being L-shaped in cross section with one leg extending along the strap and having a strap-engaging distal end portion and another leg extending rearwardly away from the strap, the latch members being relatively rigid so that each latch member moves as a unit;

each of the latch members being mounted at a central portion to the body through torsion bars which extend laterally of the latch members and which bias the strap-engaging distal end portions of the latch members against the strap to resiliently prevent reverse movement of the strap through the body;

whereby the strap can be quickly secured in place around an organ by encircling the organ with the strap, threading the ends of the strap through the openings in the clip and pulling the clip tightly against the organ, and whereby the strap can be quickly disengaged from the organ by pressing the other leg of at least one of the latch members and drawing at least one of the ends of the strap from the openings in the clip.

2. A surgical clamp according to claim 1 wherein said latch members are arranged in opposed direction for engaging the same side of said strap.

3. A surgical clamp according to claim 2 wherein said same strap side has adjacent transverse grooves for receiving said latch members.

4. A surgical clamp according to claim 1 wherein an opposite side of said strap is an organ engaging side having longitudinal grooves defining transversely spaced longitudinal ribs.

5. A surgical clamp according to claim 1 wherein each latch member includes a transverse ridge for biting into said strap and normally preventing reverse movement of said strap through said openings.

6. A surgical clamp according to claim 1 wherein each latch member is an integral part of said clip.

7. A surgical clamp according to claim 6 wherein each latch member is displacable to a strap releasing position by said strap as said strap passes through a respective one of said openings.

8. A surgical clamp according to claim 1 wherein the strap-engaging distal end portion of said latch members comprises a transverse ridge and said strap has transverse grooves which receive said transverse ridge.

9. A surgical clamp according to claim 1 and further comprising a stop on the body to limit the rational movement of the latch members away from the strap.

10. A clip for simultaneously holding two ends of a strap, said clip comprising a molded plastic member having a body with two adjacent parallel strap receiving openings therethrough, and each of said openings has projecting thereunto a latch member for engaging a side of the strap to prevent reverse movement of such strap through each of said openings, said latch member is L-shaped in cross section with one leg extending parallel to the opening and having a strap-engaging distal end portion, and another leg with a latch member extending rearwardly away from the opening, the latch member being relatively rigid so that each latch member moves as a unit, the latch members being mounted at central portions thereof to the body through torsion bars which extend laterally of the latch members, the torsion bars biasing the latch members to a rotational position such that the strap-engaging distal portions extend into the openings for engaging the strap passing therethrough;

whereby the clip can be easily mounted on the strap by passing the ends of the strap through the openings to latch the strap into place and can be easily released from the strap by depressing the other leg of the latch member to rotate the latch members away from the openings.

11. A clip according to claim 10 wherein each latch member includes a transverse ridge for biting engagement with a side of the strap having a plurality of transverse ribs.

12. A clip according to claim 10 wherein each latch member is integrally formed with the clip body.

13. In a surgical procedure on an organ a method comprising the steps of:

encircling a portion of such organ with a strap having a first side and a second side and two ends;

applying a single clip to the two ends, the clip comprising a body portion with two adjacent openings therethrough and a resiliently biased latch member in each of the openings;

inserting each of the two ends into the openings in a first direction;

drawing the two ends through the clip body in the first direction to tighten the strap and clamp the organ to prevent flow of blood to a clamped off portion of the organ;

biasing the latch members tightly against the strap to resiliently prevent movement of the strap through the body in a second direction, opposite to the first direction;

performing a surgical operation on the organ;

disengaging at least one of the latch members from the strap to thereby disengage the strap from the organ; and removing the strap from the organ.

14. The method of claim 13 wherein the latch member further comprises a first leg having a strap engaging distal end portion, and a second leg comprising a release member, the strap engaging distal end portion engaging the strap to prevent movement of the strap in the second direction, and wherein the step of disengaging at least one of the latch members is performed by pressing against the release member to disengage the strap engaging distal end portion from the strap.

15. The method of claim 13 wherein the first side of the strap has a plurality of transverse grooves and each of the latch members has a groove engaging ridge, and wherein the step of biasing the latch members comprises forcing at least one of the engaging ridge into one of said transverse grooves to prevent movement of the strap ends in the second direction.

16. The method of claim 15 wherein each of the latch members further comprises a release member for releasing the latch member from engagement with one of said transverse grooves, and the step of disengaging at least one of the latch members is performed by depressing the release member.

17. The method of claim 16 wherein each of the latch members further comprises a first leg mounting the groove engaging ridge, a torsional mount located between the release member and first leg and mounting the latch member to the body, the release member and the first leg being generally transverse to each other, and wherein the step of disengaging at least one of the latch members comprises pressing against the release member to rotate the latch member on the torsional mount whereby the groove engaging ridge of one or both latches moves away from one of said transverse grooves.

* * * * *